US007494955B2

(12) United States Patent
Charudattan et al.

(10) Patent No.: US 7,494,955 B2
(45) Date of Patent: *Feb. 24, 2009

(54) USE OF TOBACCO MILD GREEN MOSAIC VIRUS (TMGMV) MEDIATED LETHAL HYPERSENSITIVE RESPONSE (HR) AS A NOVEL METHOD OF WEED CONTROL

(75) Inventors: Raghavan Charudattan, Gainesville, FL (US); Matthew Scott Pettersen, Gainesville, FL (US); Ernest Hiebert, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 840 days.

This patent is subject to a terminal disclaimer.

(21) Appl. No.: 10/755,008

(22) Filed: Jan. 8, 2004

(65) Prior Publication Data
US 2004/0162220 A1    Aug. 19, 2004

Related U.S. Application Data

(63) Continuation-in-part of application No. PCT/US02/38063, filed on Nov. 27, 2002, and a continuation-in-part of application No. 09/997,054, filed on Nov. 29, 2001, now Pat. No. 6,689,718.

(51) Int. Cl.
*A01N 63/00* (2006.01)
*A01N 25/00* (2006.01)
(52) U.S. Cl. .................................. 504/117; 504/116.1
(58) Field of Classification Search .............. 504/100, 504/117
See application file for complete search history.

(56) References Cited

U.S. PATENT DOCUMENTS

| 4,162,912 | A |   | 7/1979 | Charudattan |
| 4,223,479 | A | * | 9/1980 | Burnside ..................... 47/1.5 |
| 5,036,006 | A | * | 7/1991 | Sanford et al. ............... 435/459 |
| 5,596,132 | A | * | 1/1997 | Zaitlin et al. ................ 800/280 |
| 6,022,828 | A | * | 2/2000 | Detweiler et al. ............ 504/117 |
| 6,060,430 | A | * | 5/2000 | Johnson et al. .............. 504/130 |

OTHER PUBLICATIONS

Petterson et al. Tobacco mild mosaic virus (TMGMV) induces a lethal response in tropical soda apple (*Solanum viarum* Dunal), Phytopathology, Jun. 2001, vol. 91, No. 6 supplement, pp. S71-S72.*
Akanda, R.U. et al. "Influence of Postemergence Herbicides on Tropical Soda Apple (*Solanum viarum*) and Bahiagrass (*Paspalum notatum*)" *Weed Technol.*, (1997), vol. 11, pp. 656-661.
Bryson, C. and Byrd, J.D. (1996) "Management Strategies for Tropical Soda Apple in Mississippi," Mississippi Dept. Agric. and Commerce, Bureau of Plant Industry Information Sheet. 2 pp.
Charudattan, R. "Biological control of tropical soda apple with plant pathogens and integration of biological control with other management options," *Abst. Meet. Weed Sci. Soc. Am.*, (2001), vol. 41, p. 80.

Chisholm, S.T. et al. "Cloning of the Arabidopsis RTM1 Gene, which Controls Restriction of Long-distance Movement of Tobacco Etch Virus" *Proc. Natl. Acad. Sci.*, (2000) vol. 97, pp. 489-494.
Culver, J.N. (1997) "Viral avirulence genes." Chpt. 6. pp. 196-219 in: G. Stacy and N.T. Keen, eds. *Plant-Microbe Interactions*, vol. 2. Chapman & Hall, New York.
Culver, J.N. and Dawson, W.O. "Tobacco Mosaic Virus Elicitor Coat Protein Genes Produces a Hypersensitive Phenotype in Transgenic *Nicotiana sylvestris* Plants" *Mol. Plant-Microbe Interact*, 1991, pp. 458-463, vol. 4.
Dawson, W.O. "Tobacco Mosaic Virus Virulence and Avirulence" *Phil. Trans. R. Soc. Lond. B.*, 1999, pp. 645-651, vol. 345.
Duan, Y.P. et al. "Expression of a Single, Host Specific, Bacterial Pathogenicity Gene in Plant Cells Elicits Divison, Enlargement, and Cell Death" *Molec. Plant-Microbe Interact.*, pp. 556-560, vol. 12.
Erickson, F.L. et al. "The Helicase Domain of the TMV Replicase Proteins induces the N-mediated Defense Response in Tobacco" *Plant Journal*, pp. 67-75, vol. 18.
French, R. "Herbert Hice Whetzel (1877-1944) and the First Department of Plant Pathology in the United States," *The Newsletter of the Plant Pathology Dept. at the University of Florida* (2001), vol. 5, Issue 1, p. 3 col. 2, paragraph 1, Published by Ronald French, Gainesville, Florida.
Jurick, W. "Graduate School: A Student Perspective," *The Newsletter of the Plant Pathology Dept. at the University of Florida* (2001), vol. 5, Issue2, p. 3 col. 2, paragraphs 2-3.
McGovern, R.J. et al. "*Solanum viarum*: Weed Reservoir of Plant Viruses in Florida" *Int. J. Pest Manage.*, 1994, pp. 270-273, vol. 40.
Mullahey, JJ and Colvin, DL. (2000) "Weeds in the sunshine: tropical soda apple (*Solanum viarum*) in Florida—1999," University of Florida Cooperative Extension Serv., Inst. of Food and Agricultural Sciences, 7 pp.
Mullahey, JJ and Colvin, DL. (1993) "Tropical soda apple: A new noxious weed in Florida," University of Florida Cooperative Extension Serv., Inst. of Food and Agricultural Sciences, Fact Sheet WRS-7.
Mullahey, J.J. "Tropical Soda Apple (*Solanum viarum* Dunal), a Biological Pollutant Threatening Florida" *Castanea*, 1996, pp. 255-260, vol. 61.
Padgett, H.S. et al. "Identification of the TMV Replicase Sequence that Activates the *N* Gene-Mediated Hypersensitive Response" *Mol. Plant-Microbe Interact.*, 1997, pp. 709-715, vol. 10.

(Continued)

*Primary Examiner*—Sreeni Padmanabhan
*Assistant Examiner*—Kristie L Brooks
(74) *Attorney, Agent, or Firm*—Saliwanchik, Lloyd & Saliwanchik

(57) ABSTRACT

Tobacco mild green mosaic virus (TMGMV) induces a lethal, systemic, hypersensitive response in Tropical Soda Apple (TSA). This response could be used to kill TSA. TMGMV could be developed and used as a bioherbicide to control TSA. TMGMV is a member of the tobamoviruses, which consist of mechanically transmitted, rod-shaped, RNA viruses that are strictly plant pathogens.

32 Claims, 5 Drawing Sheets
(5 of 5 Drawing Sheet(s) Filed in Color)

OTHER PUBLICATIONS

Pettersen, M. et al. "Tobacco Mild Green Mosiac Tombamovirus Strain U2 causes a Lethal Hypersensitive Response in *Solanum viarum* Dunal (tropical soda apple)" *Abstr. Meet. Weed Sci. Soc. AM*, 2000, p. 40, vol. 84.

Pettersen, M. et al. "Tobacco Mild Green Mosaic Virus (TMGMV) induces a Lethal Hypersensitive Response in Tropical Soda Apple (*Solanum viarum* Dunal)" *Phytopathology*, 2001, pp. S71-S72, vol. 91, No. 6.

Pettersen, M. et al. "Tobacco and mild green mosaic virus induces a lethal hypersensitive response in tropical soda apple (*Solanum viarum* Dunal)," *APS. SON. MSA Joint Meeting: Meeting Menu*, Salt Lake City, Utah, Aug. 25-29, 2001, http://www.apsnet.org/meetings/2001/oral_sessions.

Purcifull, D.E. "Ouchterlony double-diffusion tests in the presence of sodium dodecyl sulfate for detection of virion proteins and virus-induced inclusion body proteins," in: *Serological Methods for the Detection and Identification of Viral and Bacterial Plant Pathogens* (1990), pp. 179-196, R. Hampton, et al., eds., APS Press, St. Paul, MN.

Saito, T. et al. "Coat protein gene sequence of tobacco mosaic virus encodes host response determinant" *Proc. Natl. Acad. Sci. of the United States of America*, 1987, pp. 6074-6077, vol. 84, Issue 17.

Shivprasad, S. et al. "Heterologous sequences greatly affect foreign gene expression in tobacco mosaic virus-based vectors" *Virology* (1999), vol. 255, pp. 312-323.

Weber, H. and Pfitzner, J.P. "$Tm$-$2^2$ Resistance in Tomato Requires Recognition of the Carboxy Terminus of the Movement Protein of Tomato Mosaic Virus" *Molec. Plant-Microbe Interactions*, 1998, vol. 11, pp. 498-503.

\* cited by examiner

USE OF TOBACCO MILD GREEN MOSAIC VIRUS (TMGMV) MEDIATED LETHAL HYPERSENSITIVE RESPONSE (HR) AS A NOVEL METHOD OF WEED CONTROL

CROSS-REFERENCE TO RELATED APPLICATIONS

This application is a continuation-in-part of U.S. Ser. No. 09/997,054, filed Nov. 29, 2001 now U.S. Pat No. 6,689,718 and International Patent Application No. PCT/US02/38063, filed Nov. 27, 2002.

FIELD OF THE INVENTION

The subject invention pertains to the field of agriculture, more particularly to the biocontrol of undesirable plant species.

BACKGROUND OF THE INVENTION

Tropical soda apple (*Solanum viarum* Dunal; TSA) is a prickly perennial weed species indigenous to South America. Introduced into Florida in 1988 it has since become one of the most serious invasive weeds in the southeastern United States (Mullahey, 1996). Tropical soda apple is designated a noxious weed under the Federal Noxious Weed Statutes. It proliferates rapidly by both sexual and asexual means. TSA is dispersed by cattle, birds, wild animals, and certain ranching and agricultural practices. In addition to being a highly competitive weed, TSA poses an additional threat as a reservoir for several economically important plant viruses (McGovern et al., 1994). TSA is currently managed by a combination of mowing and application of the chemical herbicide triclopyr (Remedy®) (Akanda et al., 1997), but alternative means of control are necessary and desirable.

SUMMARY OF THE INVENTION

All references cited herein are incorporated by reference in their entirety, to the extent not inconsistent with the explicit teachings set forth herein.

As an alternative to chemical herbicides, we searched for a suitable pathogen of tropical soda apple (TSA) for development as a bioherbicide and have discovered that Tobacco mild green mosaic virus (TMGMV) induces a lethal, systemic, hypersensitive response in TSA. TMGMV is a member of the tobamoviruses, which consist of mechanically transmitted, rod-shaped, RNA viruses that are strictly plant pathogens. The type species of Tobamovirus is Tobacco mosaic virus U1 (TMV U1), a widely distributed plant virus. Unlike TMGMV, TMV U1 and Tomato mosaic virus (ToMV, another Tobamovirus species), caused only mild, nonlethal mosaic or mottling of the TSA leaves. The a typical lethal effect of TMGMV on TSA was unexpected and is previously unknown. Also unknown was the feasibility to use TMGMV as a biocontrol for TSA.

Tropical soda apple serves as a host for TMV U1, ToMV, and TMGMV. In contrast to the mild, systemic mosaic symptoms caused by TMV U1 and ToMV, TMGMV causes rapid death of TSA. This death occurs due to a massive, systemic, hypersensitive plant response to infection by the virus. Both serological and molecular evidence confirm that TMGMV is responsible for the rapid and high rate of mortality on TSA. The age of TSA at the time of TMGMV inoculation does not affect the mortality rates, but the first expression of symptoms and first plant mortality are slightly delayed in older plants as compared to younger plants. Thus, the ability to control TSA by TMGMV is not limited by plant age. Temperature is usually not a limiting factor, although disease development will be slowed or prevented if the inoculated TSA plants are maintained continuously at 32° C. (or presumably at higher temperatures). However, under normal field conditions, a diurnal temperature fluctuation will occur and as our results indicate, TMGMV kills TSA plants under the diurnal cycle of 32/22° C. temperatures. To avoid possible adverse effects of high temperatures according to the subject invention, the TMGMV is preferably used in the field during the cooler months of spring and fall.

The host reaction of two *Capsicum annuum* cultivars indicates that, as a precaution, TMGMV should not be used in the vicinity of pepper crops. Also, since tobacco (*Nicotiana tabacum*) is a natural host to TMGMV, this virus should not be used near tobacco crops. However, it is safe to use the virus near tomato and eggplant crops.

Field trials from Hawthorne (north-central Florida) and Deseret Ranch (south-central Florida) sites confirm the excellent efficacy of TMGMV as a biological control agent for TSA. The levels of TSA control obtained with TMGMV were comparable to or better than the control levels obtained with chemical herbicides, but without the risks of chemical contamination.

Other advantages of TMGMV are first, the feasibility to produce abundant supplies of the virus by a simple, inexpensive method in susceptible tobacco; and second, the extremely small doses needed for high levels of TSA control. This virus-based bioherbicide system can be produced, developed, and registered more easily than fungal-based bioherbicides. Another important aspect of the TSA-TMGMV system is its highly novel mode of action, which is based on a systemic hypersensitive host response triggered by a gene of the virus.

For example, unlike chemical herbicides that must be applied to substantially the entire plant foliage to effectively induce plant death, the virus TMGMV needs to be inoculated into just a few leaves per plant to produce up to 99% control. There are no significant environmental constraints that will prevent virus infection. Practical methods are available for field-application of the virus. For example, such methods can be easily adopted into a statewide TSA management program.

Moreover, large quantities of the TMGMV inoculum, in accordance with the present invention, can be produced in tobacco plants. The TMGMV inoculum can then be stockpiled and applied in the field.

Accordingly, it is an object of the present invention to provide a novel method of weed control.

It is a further object of the present invention to provide a method of weed control utilizing tobamoviruses.

It is a still further object of the present invention to provide a method of weed control utilizing TMGMV.

It is a still further object of the present invention to provide a method of controlling the tropical soda apple utilizing TMGMV.

Yet another object of the present invention is the ability to easily produce TMGMV inoculum in tobacco plants, as well as to stockpile and apply the inoculum in the field.

Further objects and advantages of the present invention will become apparent by reference to the following detailed disclosure of the invention and appended photographs.

BRIEF DESCRIPTION OF DRAWINGS

The file of this patent contains at least one drawing executed in color. Copies of this patent with color drawings(s) will be provided by the Patent and Trademark Office upon request and payment of the necessary fee.

DETAILED DESCRIPTION OF THE INVENTION

Figure 1:
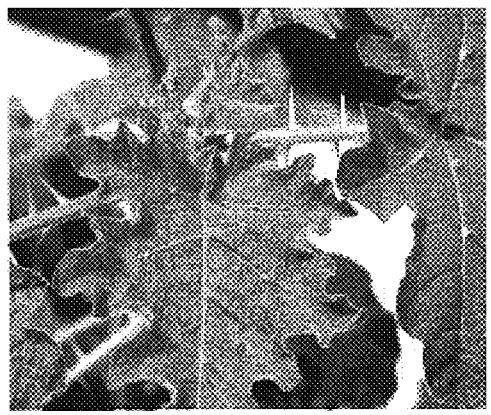
FIG. 1 is a photograph depicting the mosaic symptoms caused by TMV U1.
Figure 2:
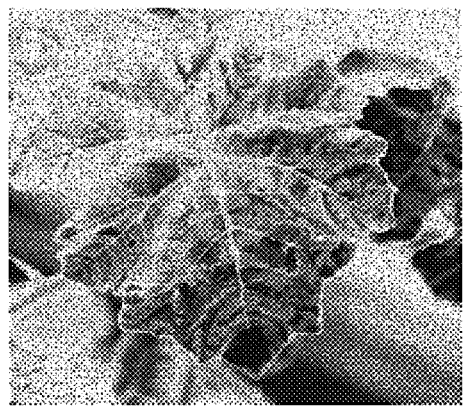
FIG. 2 is a photograph depicting the mosaic symptoms caused by ToMV.
Figure 3:
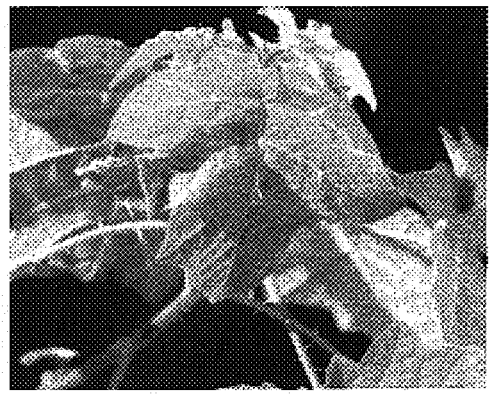
FIG. 3 is a photograph depicting the mosaic symptoms caused by TMGMV.
Figure 4:
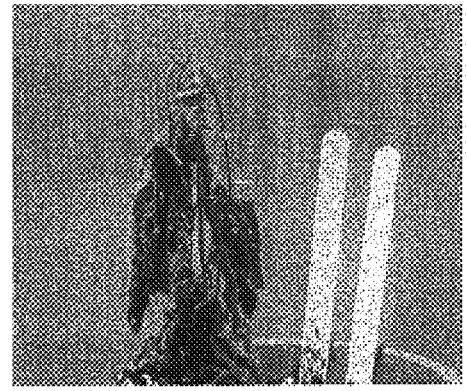
FIG. 4 is a photograph depicting the lethal systemic necrosis caused by TMGMV, two weeks post-inoculation.
Figure 5:
FIG. 5 is a photograph depicting the effect of TMGMV on 2-month-old TSA, 1-2 weeks post inoculation.
Figure 6:
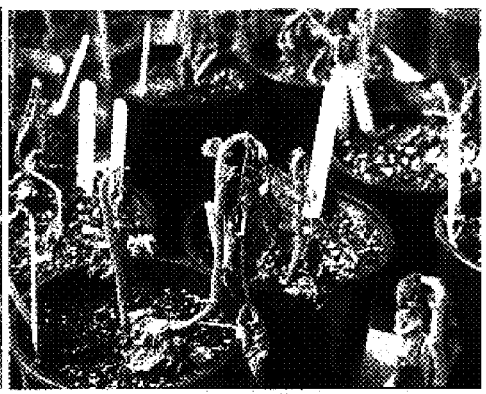
FIG. 6 is a photograph depicting the effect of TMGMV on 3-month-old TSA, 2 weeks post inoculation.
Figure 7:
FIG. 7 is a photograph depicting the effect of TMGMV on 7-month-old TSA, approximately one-month post inoculation.

Following are examples which illustrate procedures for practicing the invention. These examples should not be construed as limiting. All percentages are by weight or numbers and all solvent mixture proportions are by volume unless otherwise noted.

EXAMPLE 1

Virus Isolates

Three tobamovirus isolates, Tobacco mild green mosaic virus (TMGMV), Tobacco mosaic virus ((TMV U1), and Tomato mosaic virus (ToMV) are used. These viruses are maintained in infected, frozen, tobacco tissue in the plant virus collection at the Plant Pathology Department, University of Florida, Gainesville.

Plant Materials

*Nicotiana tabacum* L. cultivar Turkish Samsun nn (tobacco) is used as the susceptible host to maintain the tobamovirus species and produce their inocula. Tobacco (*Nicotiana tabacum* L.) cv. Turkish Samsun NN, a TMV-resistant variety, which develops hypersensitive local lesions on leaves, in response to infection by these tobamoviruses, is used to assay the viruses for efficacy of their inocula. The TSA seeds used in this study are collected from TSA-infested sites in southern Florida, primarily in Immokalee, Fla.

The tobacco and TSA seeds are sown at a depth of about 3-4 mm in seedling trays containing Metro-Mix® 300 potting soil (Scotts-Sierra Horticultural Products Company, Marysville, Ohio). At 1- to 2-leaf stage, the seedlings are transplanted singly into individual 6-cm-diameter pots. The plants are grown under natural sunlight in a greenhouse. To reduce the risk of cross contamination, the tobacco and TSA plants inoculated with each tobamovirus species are maintained in separate greenhouses.

Pathogenicity Testing of TMV U1, ToMV, and TMGMV on TSA

The susceptibility of TSA to TMV U1, ToMV, and TMGMV is determined in comparison with the reaction of susceptible and resistant tobacco to these viruses. Five susceptible (nn) and two resistant (NN) tobacco plants are manually inoculated with inoculum suspension prepared by triturating about 20 mg of each frozen tobamovirus sample in 0.02 M sodium phosphate buffer (pH 7.2). The susceptible tobacco plant also serves as the inoculum source for all subsequent experiments. About 20 mg of carborundum (320 grit) is added to the buffer-virus preparation to serve as an abrasive. The TSA plants (approx. 60-day-old) are inoculated by gently rubbing the leaf on the abaxial midrib from leaf tip to leaf base with a piece of cheesecloth soaked in inoculum. The prickles on the midrib typically snap easily in this direction. The control TSA plants are treated similarly but with buffer+ carborundum only. The trial is performed two times, each with 10 plants for the inoculated treatment and two plants for the control.

Referring now to FIGS. 1-4, all three tobamoviruses infect TSA. In resistant Turkish Samsun NN plants inoculated with the tobamoviruses, hypersensitive local lesions develop in the leaves in 3 to 4 days. In comparison, the susceptible nn tobacco develop mild, systemic mosaic symptoms at 9, 14, and 10 days after inoculation with TMV U1 (FIG. 1), ToMV (FIG. 2), and TMGMV (FIG. 3), respectively. The first symptom expression in TSA inoculated with TMGMV appears in 6-8 days, compared with an average of 13 and 16 days for TMV U1 and ToMV. TMVU1 and ToMV cause the same systemic mosaic symptoms in leaves of inoculated TSA plants in both trials.

Compared with TMV U1 and ToMV, TMGMV produces a devastating systemic necrosis (FIG. 4). In two trials, 100% of the inoculated TSA plants are killed by a systemic hypersensitive response (HR). Mock-inoculated control TSA plants remain healthy. Leaf drop and dieback occurs 5 to 6 days after the onset of first symptoms. After 6 days, severe wilting occurs with dark-gray to black necrotic lesions on inoculated leaves. The wilted plants are kept watered to determine whether the plants would regenerate by producing suckers. Three of the TSA plants that die down to the soil level produce suckers and regenerate. Initially, the new suckers are asymptomatic, but after a few weeks, these seemingly healthy suckers die from systemic HR.

SDS Immunodiffusion Tests

The presence or absence of the viruses in plant tissues and their identities are confirmed with the aid of immunodiffusion tests. These tests are done as follows: At approximately 1-3 weeks after inoculation, newly developed leaves from virus-inoculated and control TSA plants are collected, and their saps extracted with the aid of a mechanical sap extractor. The saps are diluted 1:1 in sterile water and then further diluted to 1:1:1 volume with 3% sodium dodecyl sulfate (SDS) prior to loading in immunodiffusion plates. The immunodiffusion tests are done as described by Purcifull (1990) using 0.8% Noble agar, 0.5% SDS and 1.0% $NaN_3$. TMV U1, ToMV, and TMGMV antisera are obtained from the collection of antisera available at the Plant Pathology Department, University of Florida.

In immunodiffusion tests, the TMGMV antiserum produces identical precipitin bands with antigens from the TMGMV-inoculated Turkish Samsun nn tobacco (TMGMV-Tobacco) and TSA (TMGMV-TSA), confirming that the same virus is present and responsible for the observed symptoms in both plants. The TMGMV antiserum does not react with antigens prepared from healthy TSA plants. The TMV U1 antiserum produces precipitin lines with antigens from TMV U1-inoculated Turkish Samsun nn tobacco (TMV U1-Tobacco) and TMGMV-inoculated TSA (TMGMV-TSA) plants. The precipitin bands spur over, indicating partial identity of the two antigens. Likewise, ToMV-TSA and TMGMV-TSA antigens show partial identity against ToMV antiserum. The ToMV antiserum reacts with ToMV-inoculated Turkish Samsun nn tobacco (ToMV-Tobacco) and TSA (ToMV-TSA) and produces precipitin bands that spur over in reactions with ToMV-TSA and TMV U1-TSA antigens. The preimmune blank antisera do not react with antigens from tobacco or TSA infected with any of the tobamoviruses.

Experimental Culture of TMGMV vs. a cDNA-cloned Virus

The TMGMV isolate used in this study is compared against a cDNA-derived TMGMV (cDNA clone) to confirm that our isolate consists of a pure culture. The cDNA clone is provided by W. O. Dawson, Citrus Research and Education Center, IFAS, University of Florida, Lake Alfred. Inocula of our TMGMV isolate and the cDNA-derived virus are produced in Turkish Samsun nn tobacco. Each virus inoculum is manually inoculated on five TSA and three Turkish Samsun NN tobacco plants. The plants are 45- to 60-day old transplants at the time of inoculation. This experiment is done twice to confirm the results.

Both the cDNA cloned and the test isolate of TMGMV multiplied in Turkish Samsun nn tobacco and inoculated into TSA produce initial symptoms on TSA at 6 days after inoculation. All plants in trial 1 inoculated with the test TMGMV isolate or the cDNA-derived virus die by 10 days after inoculation. In Trial 2, the TMGMV test isolate completely kills TSA plants by 10 days, whereas the cDNA-derived virus kills two plants by the 10th day. The remaining three TSA plants inoculated with the cDNA-derived virus have systemic necrosis, and newly emergent leaves develop mosaic and necrotic flecks. These plants are severely stunted and lignified throughout the main stems and branches.

Effect of Plant Age on TMGMV Disease Development

The effect of TSA plant age on the susceptibility of this plant to TMGMV is tested. This experiment is done twice with six age categories of greenhouse-grown TSA plants: less than 1-month, 1-month, 2-months, 3-months, 7-months, or more than 1-year old. Plants for the age-effect experiment are grown in Metro-Mix® 300 potting medium amended with Multicote® (15-15-15:N-P-K, TRI-Pro Inc., Apopka, Fla.). TSA seed is sown on a monthly basis prior to the experiment, except for the more-than-1-year category. Plants for this category come from those that have been previously maintained in a greenhouse. There are 6 to 10 plants for inoculated treatments and 2 for controls. Plants of all age categories are inoculated manually, as described above, with the TMGMV inoculum produced in Turkish Samsun nn tobacco.

The plants are monitored for symptom development over time. Plant death is defined as the complete defoliation and severe necrosis of aboveground parts. The time of appearance (in days) of the first symptoms and time of first death are recorded for each age group. The data are analyzed using SAS (Statistical Analysis Systems, Cary, N.C.) by analysis of variance. Significant means are separated by Duncan's multiple range test.

Figure 8:
FIG. 8 is a photograph depicting mock inoculated (buffer only) control plants, 2 weeks post inoculation.

Referring now to FIGS. 5-8, the age of the TSA plant influences the speed of symptom development (i.e., day when first symptom development appears) as well as plant mortality (i.e., day when the first plant death is noted). (Table 1). The first symptoms are foliar local lesions. This is followed by severe wilting and necrosis on the stems and petioles, and complete collapse of the leaf tissues. Within one month after inoculation, 100% of the inoculated TSA plants die in both trials. Symptoms appear sooner in plants less than 3-months-old (FIGS. 5 and 6) compared to 7-months-old (FIG. 7) or older-than-1-year plants. (Table 2). In trial 1, older-than-1-year plants develop symptoms later than 7-month-old plants. In trial 2, this order is reversed. TSA plants less than 1-month-old and 3-month-old are killed most quickly compared with older plants, which took twice as long to die. Suckers emerge from three treated plants: a healthy sucker emerges in the first trial from a 3-month-old plant. This sucker grows for about 2 to 3 months and then dies from systemic HR. A second sucker then emerges from the same plant, grows for about 5 months, and then dies from systemic HR. No further suckers emerge from this plant, indicating total kill. The two remaining plants that sucker are the 1-month and 7-months old. These suckers are severely stunted (max. height of ca. 10-15 cm) and leaves on these suckers have necrotic lesions. Three months later, leaves from each of these mosaic-displaying suckers are individually triturated and the sap inoculated into three healthy 4- to 5-month-old TSA plants. About one week after inoculation, the plants develop systemic necrosis accompanied by leaf abscission. In the following 3 weeks, newly emerged leaves produce the same mosaic symptoms as in the suckers. Over time, systemic lignification occurs, producing a woody appearance on the main stem and branches. The prickles on the stem and branches become brittle and many on the leaves display signs of necrosis. Control plants inoculated with buffer only show no symptoms after 2 weeks (FIG. 8).

TABLE 1

Analysis of Variance of the Effects of TSA Age Groups on the Day of First Symptom Appearance and Day of Death After Inoculation with TMGMV

| | | First symptom | | Death Day MS | |
|---|---|---|---|---|---|
| Treatment | df | MS Means | F-value | df | Means | F-value |
| Trial 1 Age Groups | 5 | 49.95 | 152.97* | 5 | 136.37 | 44.7* |
| Trial 2 Age Groups | 5 | 49.27 | 284.0* | 5 | 640.91 | Infinity* |

Data for Trial 1 and Trial 2 were analyzed separately.
df = degrees of freedom
*$P < 0.0001$.

TABLE 2

Effect of Plant Age on First Symptom Appearance and First Death of Plants Inoculated with TMGMV $(P > 0.0001)^a$

| | First symptom appearance | | | Time to death | | |
|---|---|---|---|---|---|---|
| | Plant Age[b] | N[c] | Mean[d] | Plant Age[b] | N[c] | Mean[d] |
| Trial 1 | >12 | 6 | 10.0 a | >12 | 6 | 21.5 a |
| | 7 | 10 | 9.4 b | 7 | 10 | 18.0 b |
| | 3 | 10 | 5.0 c | 3 | 10 | 13.0 c |
| | 2 | 10 | 5.0 c | 2 | 10 | 13.0 c |

TABLE 2-continued

Effect of Plant Age on First Symptom Appearance and First
Death of Plants Inoculated with TMGMV (P > 0.0001)[a]

|  | First symptom appearance | | | Time to death | | |
|---|---|---|---|---|---|---|
|  | Plant Age[b] | N[c] | Mean[d] | Plant Age[b] | N[c] | Mean[d] |
|  | 1 | 9 | 5.0 c | 1 | 9 | 13.0 c |
|  | <1 | 10 | 4.8 c | <1 | 10 | 10.0 d |
| Trial 2 | >12 | 5 | 6.7 | >12 | 5 | 25.0 b |
|  | 7 | 10 | 11.6 | 7 | 10 | 30.0 a |
|  | 3 | 10 | 6.0 | 3 | 10 | 12.0 c |
|  | 2 | 10 | 6.0 | 2 | 10 | 12.0 c |
|  | 1 | 10 | 6.0 | 1 | 10 | 12.0 c |
|  | <1 | 10 | 6.0 | <1 | 10 | 10.0 d |

[a]Means separated by Duncan's multiple range test.
[b]Plant age in months.
[c]N = number of replicates (TSA plants).
[d]Mean number of days to first symptoms or first plant death.

Effect of Temperature on TMGMV Disease Development

Since virus replication and disease development could be temperature-controlled, an experiment is conducted to determine the effect of temperature on TMGMV disease development in TSA. Three temperature regimes, continuous 18° C., continuous 32° C., and alternating 32/22° C., are established in controlled-environment plant growth chambers. All treatments have a 12-hour photoperiod with 250 μE/m$^2$/s illumination provided by a combination of fluorescent and incandescent light bulbs. Plants of same ages are tested at each temperature regime. Plants in the 18° C. experiments are 5 and 7 months old for the first and second trials, respectively. Plants in the 32° C. experiment are 5 and 6 months old. For the 32/22° C. treatments, 3- to 4-month-old plants are used. The plants are manually inoculated with TMGMV and symptoms are recorded daily starting at 4 or 5 days after inoculation. The plants are kept in the chambers at the respective temperatures for 30 days after inoculation, except as stated below for plants at 32° C.

The temperature of the experiment has an impact on disease development (Table 3). TMGMV kills 100% of the inoculated TSA plants incubated at 18° C. and 32/22° C. in both trials. No symptoms develop at 32° C., possibly due to restriction of virus movement and/or multiplication at this temperature. At 18° C., the first symptoms appear in 7 and 9 days, respectively, in the first and second trials. At 32/22° C., the first symptoms appear in 7 and 10 days, respectively, in the two trials.

TABLE 3

Analysis of Variance of the Effect of Different Incubation
Temperatures on First Symptom Appearance and Day of
Death for Trials 1 and 2[a]

|  | First symptom | | | First death | | |
|---|---|---|---|---|---|---|
|  | df | MS Means | F-value | df | MS Means | F-value |
| Trial | 1 | 83.36 | 119.22* | 1 | 20.33 | 3.71 NS |
| Temp | 1 | 0.312 | 0.45 NS | 1 | 1282.67 | 234.18* |
| Trial * Temp | 1 | 10.03 | 14.35* | 1 | 86.11 | 15.72* |

[a]Three temperature regimes were tested: continuous 18° C., alternating temperatures of 32° C. (day) and 22° C. (night). The high temperature incubation trials were not included in the analysis due to lack of symptom development at 32° C. There were 8-10 plants per trial.
*P < 0.0001.
NS = not significant.

At 18° C. (low temperature), the TSA plants develop a high density of local lesions on the leaves. Fewer, scattered, local lesions develop 32/22° C. The local lesions appear on inoculated leaves as well as on noninoculated, newer leaves. Leaves with local lesions also develop severe chlorosis. The local lesions gradually coalesce and cover the entire leaf, but the stems remains mostly green with scattered necrotic spots. Plants die approximately 1 month after inoculation in both trials. The control plants remain healthy during both trials.

The asymptomatic plants from the 32° C. treatment are removed from this temperature after 17 days and placed in a greenhouse at 25±3° C. Five to 6 days after placement at 25±3° C., these plants develop systemic but nonlethal necrosis in 5 to 6 days. Several leaves absciss and others have wilted petioles and flaccid laminae. The older leaves gradually die and newly developing leaves express epinasty and mosaic similar to those seen on the suckers in the age-effect experiment. The new leaves are stunted and have necrotic flecks; even the prickles on the leaves are often necrotic. Over several weeks, the stems and branches gradually become lignified and develop a woody appearance throughout. Fruiting on these plants is limited or nonexistent and fruits that develop are destroyed by necrosis. Most plants die within 6-12 months after they are removed from 32° C. These results are consistent in the both trials.

The symptoms seen in TSA plants kept at 32° C. are typical of the attenuated symptom expression known in many plant-virus interactions. When three of these plants exhibiting this attenuated disease expression are reinoculated with TMGMV, they produce relatively more chlorosis and necrotic foliar lesions than seen at the time of inoculation, but do not die. This suggests the possibility that a milder TMGMV strain may have been selected at the high temperature and this milder strain may be cross-protecting the plant against the second, challenge-inoculation with the test isolate of TMGMV.

Reaction of Some Members of the Solanaceae to TMGMV

Reaction of some plants belonging to the Solanaceae family, to which TSA belongs, is studied to understand the range of nontarget plants that TMGMV might attack and the types of possible host reactions that might occur. Seeds of test plants are acquired from the Plant Introduction Station, Iowa State University, Ames, Iowa, except for tomato (*Lycopersicon esculentum* cv. Better Boy) plants that are obtained from Alachua Feed and Seed, Gainesville, Fla. Seeds are sown in Metro-Mix® 300 potting medium amended with Multicote®. One month after seedlings emerge, individual plants are transplanted into 6-cm pots containing Metro-Mix. The tomato seedlings are planted at this time. At inoculation, the plants are 1- to 3-month old after transplantation. Within each treatment, the plants are of the same age. The plants are manually inoculated as described previously and observed for symptoms. There are four plants in each inoculated treatment and two in the controls. The experiment is performed two times.

A reliable test to detect viral infections and identify the virus present is the indirect enzyme-linked immunosorbant assay (ELISA). This assay is used to confirm the presence and identity of TMGMV infections in inoculated plants. For ELISA, newly developed leaves from both inoculated and healthy controls are collected 2 to 3 weeks after inoculation and ca. 5 g of the leaf tissue are crushed in a mechanical sap extractor and diluted to a 1:1 volume with sterile deionized water. This crude sap sample is diluted 1:10 with an extraction buffer ($Na_2SO_3$, polyvinylpyrrolidone-40, bovine serum albumin, phosphate buffered saline, and 0.05% Tween-20

[PBST], pH 9.6). TMGMV antisera are diluted 1:1000 in PBST at pH 7.4. Whole-molecule goat anti-rabbit alkaline phosphatase conjugate purchased from Sigma Chemical Co. (St. Louis, Mo.) is diluted 1:20,000 and reacted with the TMGMV-TSA-buffer extract. The absorbance values of the reaction mixture are recorded at (405 nm) at 15-minute intervals with a spectrophotometer. A sample is considered positive if the average of three reaction wells per sample is greater or equal to three times the value of healthy control value. A positive ELISA reading indicates the presence of the virus in the inoculated plants, irrespective of the expression of visible symptoms.

Among the members of the Solanaceae family screened, some Solanum species and *Capsicum annuum* cultivars are susceptible to TMGMV. (Table 4). Approximately one-third of the species tested are susceptible, but each reacts differently to TMGMV. Eighty percent of the susceptible species produce a nonlethal hypersensitive response (HR), which is a resistance response.

TABLE 4

Reaction of Some Solanum Species to TMGMV

| Host species | Absorbance values (405 nm)[a] Treated | Control | Host Reaction[b] |
|---|---|---|---|
| *C. annuum* L. (Jalapeno) | 1.09 | 0.303 | SHR+ |
| *C. annuum* cv. California Wonder | | | SHR+ |
| *L. esculentum* Mill. cv. Better Boy | | | |
| *S. acerifolium* Dunal | 0.398 | 0.277 | |
| *S. aculeatissimum* Jacq. | 0.186 | 0.18 | |
| *S. aethiopicum* L. | 0.08 | 0.09 | |
| *S. americanum* Mill. | 0.02 | 0.07 | LHR |
| *S. anguivi* Lam. | 0.02 | 0.03 | LHR |
| *S. atropurpureum* Schrank | | | |
| *S. aviculare* G. Forst. | | | |
| *S. capsicoides* All. | | | |
| *S. caripense* Dunal | | | |
| *S. ciliatum* Lam. | | | |
| *S. elaeagnifolium* Cav. | 0.02 | 0.03 | |
| *S. ferox* auct. = *S. lasiocarpum* Dunal | | | |
| *S. gilo* Raddi = *S. aethiopicum* L. | | | LHR |
| *S. incanum* L. | | | |
| *S. linnaeanum* Hepper & P.M.L. Jaeger | | | |
| *S. macrocarpon* L. | | | M+ |
| *S. mammosum* L. | | | |
| *S. melongena* L. | | | |
| *S. nigrum* L. var. villosum L. = *S. villosum* Mill. | 0.44 | 0.06 | +NS |
| *S. nodiflorum* Jacq. = *S. americanum* Mill. | 0.14 | 0.09 | LHR |
| *S. pseudocapsicum* L. | 0.015 | 0.02 | LHR |
| *S. rostratum* Dunal | 0.19 | 0.03 | +NS |
| *S. sessiliflorum* Dunal | | | LHR |
| *S. sisymbriifolium* Lam. | 0.05 | 0.03 | |
| *S. spinosissium* Lodd. ex G. Don, nom. nud. | 0.2 | 0.01 | M+ |
| *S. stramoniifolium* Jacq. | 0.06 | 0.04 | |
| *S. suaveolens* Kunth & C.P. Bouche | 0.64 | 0.47 | |
| *S. tampicense* Dunal | | | |

[a]Samples screened by indirect ELSIA. Virus-free control plants in each treatment remained asymptomatic and healthy.
[b]Host reactions: + = positive reading by ELISA, blank space = negative reading.
LHR = localized hypersensitive response,
SHR = systemic hypersensitive response,
M = mosaic symptoms,
NS = no symptoms.

*Solanum americanum, S. anguivi, S. gilo, S. nodifolium, S. pseudocapsicum*, and *S. sessilifolium* produces localized HR. The presence of TMGMV infection is detected by indirect ELISA in *S. macrocarpon, S. nigrum, S. rostratum*, and *S. spinosissimum*. Of these, *S. nigrum* and *S. rostratum* do not develop visible symptoms, while *S. macrocarpon* and *S. spinosissimum* develop mosaic symptoms. The cultivated pepper species *Capsicum annuum* (California Wonder and Jalapeño) develops systemic HR. In the first trial, two California Wonder (bell pepper) plants were killed within 2 to 3 weeks after inoculation. In the second trial, one jalapeño pepper plant was killed. The remaining *C. annuum* plants have necrotic lesions on leaves and stems, minor leaf distortion, fruit malformation, and stunting. *Lycopersion esculentum* cv. Better Boy (tomato) and *Solanum melongena* (eggplant), as well as the remaining Solanum species, are immune and therefore nonhosts to TMGMV. This is confirmed by the indirect ELISA absorbance values for leaf extracts (antigen samples) from corresponding inoculated and control plants (Table 4).

Field Trials of Efficacy of TMGMV as a Herbicide for TSA

In a first set of field trials, the inoculum is prepared by triturating up to 10.0 g vacuum-dried, TMGMV-infected Turkish Samsun nn tobacco leaf tissue (preferably 0.5, 1.0, 1.5, and 3.0 g) in 10-20 ml of sodium phosphate buffer (pH 7.2). The extracted samples are then filtered by means known in the art, for example, strained through sterile cheesecloth into capped vials. At the time of inoculation, the virus-buffer mixture is poured into 1 liter of sterile deionized water. One gram of carborundum (320 grit) was added to each liter to serve as an abrasive. To prevent contamination of the controls, the virus-free control treatments are applied first followed by the virus treatments.

The efficacy of TMGMV as a bioherbicide for TSA is established through field trials. These trials are conducted at two sites. Field Site No. 1 is in a 5-ha cattle pasture near Hawthorne, Fla., which has a moderate density of TSA infestation. The TSA plants in this field range in maturities from small seedlings to large-canopied, fruit-bearing plants. The trial is performed two times at this site.

Effects of two application methods and two inoculum levels are compared in trail 1. The application methods consist of hand inoculation and pressure-infiltration, for example, with the aid of a $CO_2$-propelled backpack sprayer. The sprayer is set at pressure between 20 and 100 psi, preferably 60 psi and has a Teejet 5500 nozzle. To insure infection, the nozzle is pressed against the adaxial surface of the TSA leaves, while spraying. After infiltration, the inoculated spots are inspected for signs of water soaking. The inoculum levels consist of 0.5 or 1.0 gram of TMGMV-infected Turkish Samsun nn tissue extracted in one liter of buffer for the pressure-infiltrated treatments in trial 1 and 1.5 and 2.0 g in trial 2. Hand-inoculated treatment is done as described previously by rubbing the inoculum on the abaxial leaf surface. Five to eight leaves per plant are inoculated by each inoculation method. There are 30 plants per treatment. Each plant is measured for plant height and canopy diameter. Canopy size is determined by taking the average of two measurements (the longest width and the width perpendicular to the longest width).

The inoculum suspension is prepared by triturating up to 10.0 g vacuum-dried, TMGMV-infected Turkish Samsun nn tobacco leaf tissue (preferably 0.5, 1.0, 1.5, and 3.0 g) in 10-20 ml of sodium phosphate buffer (pH 7.2). The extracted samples are then filtered by means known in the art, for example, strained through sterile cheesecloth into capped vials. At the time of inoculation, the virus-buffer mixture is poured into 1 liter of sterile deionized water. One gram of carborundum (320 grit) was added to each liter to serve as an abrasive. To prevent contamination of the controls, the virus-free control treatments are applied first followed by the virus treatments.

After 5 days, the plants are rated for symptom appearance and then rated at 2- to 3-day intervals. The data are analyzed using the SAS program (Statistical Analysis System, Cary, N.C.) by analysis of variance. Significant means are separated by Duncan's multiple range test and Tukey's Honest Significant Difference test.

Two additional field trials (Field Site Nos. 2 and 3) are conducted at the Deseret Cattle and Citrus Company, St. Cloud, Fla. Field Site No. 2 is located in a pasture, under a cypress hammock and contains 100 plants each for the inoculated and control treatments. Field Site No. 3 is located in an open pasture and contains 70 plants each for the inoculated and control treatments. The plants are randomly assigned treatments and identified with colored flags or plastic labels. The inoculum is prepared in the same manner as the trials at Field Site No. 1, but consists of 1.5 g of TMGMV-infected leaf tissue per liter concentration. Only the pressure-infiltration method is used to inoculate the plants at Field Site No. 2. Data are recorded at 14, 25, and 51 days after inoculation and analyzed using the SAS program.

At Field Site No. 1, TSA plants of various sizes and maturities are killed following inoculation with TMGMV. (Table 5). The method of inoculation or inoculum concentration does not affect disease development or plant kill. Both the hand-inoculation and pressure-infiltration methods are equally effective. (Table 6). In addition, the inoculum concentrations of 0.5, 1.0, 1.5, and 3.0 g/liter are equally effective. The canopy diameters of plants inoculated in trials 1 and 2 range from 0.5-2.0 m and plant height ranged from 18-110 cm. A regression analysis indicates no correlation between plant size and first appearance of symptoms or first mortality.

TABLE 5

Analysis of Variance of the Effect of TMGMV Inoculation on Day of First Symptom Expression and Day of First Death in Field Trials 1 and 2 (P > 0.0001) at Field Site No. 1.

| | Trial 1 | | | Trial 2 | |
|---|---|---|---|---|---|
| df | MS Means | F-value | df | MS Means | F-value |
| | First symptom | | | First symptom | |
| 3 | 7.34 | 881 | 3 | 7.26 | 450.68 |
| | Days until death | | | Days until death | |
| 3 | 5.65 | 72.89 | 3 | 5.99 | 90.17 |

TABLE 6

Effects of TMGMV inoculation on TSA Plants in Field Trials 1 and 2 (P > 0.0001) at Field Site No. 1.

| Percentage of TSA plants expressing symptoms | | | | | |
|---|---|---|---|---|---|
| Field trial 1[a] | | | Field trial 2[b] | | |
| % Inoculated plants | N[c] | Treatment[d] | % Inoculated plants | N[c] | Treatment |
| 100.0[a] | 30 | 0.5 g/liter infilt. | 100.0[a] | 32 | 1.5 g/liter infilt. |
| 100.0[a] | 30 | Hand inoc. | 97.0[a] | 32 | 3.0 g/liter inilt. |
| 97.0[a] | 30 | 1 g/liter infilt. | 97.0[a] | 30 | Hand inoc. |
| 0.0[b] | 30 | Control | 0.0[b] | 30 | Control |

TABLE 6-continued

Effects of TMGMV inoculation on TSA Plants in Field Trials 1 and 2 (P > 0.0001) at Field Site No. 1.

| Percentage of mortality of TSA plants | | | | | |
|---|---|---|---|---|---|
| % inoculated plants | N[c] | Treatment | % inoculated plants | N[x] | Treatment |
| 93.0[a] | 30 | 0.5 g/liter infilt. | 97.0[a] | 32 | 1.5 g/liter infilt. |
| 90.0[a] | 30 | Hand inoc. | 83.0[a] | 32 | Hand inoc. |
| 87.0[a] | 30 | 1 g/liter infilt. | 94.0[a] | 30 | 3.0 g/liter infilt. |
| 0.0[b] | 30 | Control | 0.0[b] | 30 | Control |

[a]Based on Tukey's HSD test.
[b]Based on Duncan's multiple range test.
[c]Number of plants per treatment.
[d]Amount of inoculum and application method: infilt. = plants inoculated by pressure-infiltration of inoculum on the adaxial leaf surface. Hand inoc. = Inoculum applied to abaxial leaf surface by hand-rubbing with inoculum containing leaf extract; the precise amount of inoculum is not characterized. Control = control plants mock-inoculated with buffer only.

Figure 9A:
FIG. 9A is a photograph depicting manually inoculated plants prior to symptom expression.
Figure 9B:
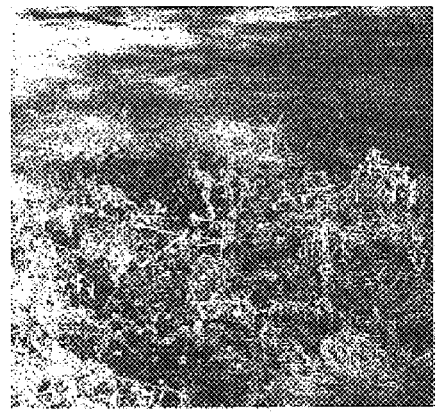
FIG. 9B is a photograph depicting the manually inoculated plants of FIG. 9A, two-three weeks post inoculation.
Figure 10:
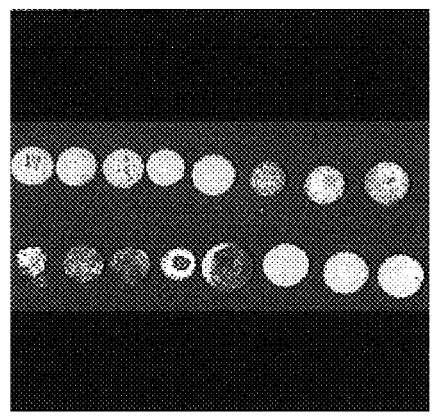
FIG. 10 is a photograph depicting the effects of TMGMV on TSA fruits. Top row shows fruits from control plants; bottom row shows fruits from inoculated plants.

Referring now to FIGS. 9A and 9B, the first symptoms on inoculated plants in the field are foliar lesions, followed by systemic necrosis. No suckers appear during the 2-month period when the data are collected. Many fruits, still maturing at the time of inoculation, exhibit necrotic symptoms, and most of the necrotic fruits are shriveled and withered. (FIG. 10). Fruits that are mature at the time of inoculation remain healthy even though the plant has necrosed. Healthy, mature fruits collected from two surviving plants have viable seeds. The mock-inoculated control plants remain healthy.

The efficacy of TMGMV as a biological control agent is confirmed also in the Deseret Ranch field trials (Table 7). At Field Site No. 2, disruptions from cattle congregating under the hammock and flooding due to heavy rainfall prevent data collection at this site beyond 14 days after inoculation. On day 14, the remaining plants, 47 inoculated TSA plants and 35 control plants, are rated. Of the inoculated plants, 59.5% are killed by TMGMV by this day compared with 5.7% mortality among the control plants. The remaining inoculated plants have foliar lesions and signs of necrosis.

TABLE 7

Percentage of TSA Plants Killed by TMGMV at Field Site Nos. 2 and 3.

| | | Days after inoculation | | |
|---|---|---|---|---|
| Trial sites[a] | Treatment | 14 | 25 | 51 |
| Field Site No. 2 | Inoculated | 59.5 A[b] | NA | NA |
| | Control | 5.7 B | NA | NA |
| Field Site No. 3 | Inoculated | 3.0 A | 75.0 A | 88.4 A |
| | Control | 0.0 A | 1.6 B | 1.6 B |

[a]At Field Site No. 2, the trial is abandoned after 14 days due to disruption of the site by cattle and flooding. The data are from 47 inoculated and 35 control plants. Field Site No. 3 has 70 plants per treatment.
[b]Within a column, numbers followed by different letters are significantly different at P = 0.01 using Duncan's multiple range test.

At Field Site No. 3, by 25 days, 75% of the inoculated TSA plants and 1.6% of the control plants are killed. No suckers emerge from either the treated or the control plants. By day 51, 88.4% of the inoculated plants have died compared to 1.6% of the control plants. The control plants probably die due to cross-contamination by TMGMV or from other biotic or abiotic causes.

Another application method according to the subject application consists of over-the top spraying application on the entire plant. This over-the-top application may be conducted without the placement of the spray nozzle on the leaves of the TSA plants to insure infection. After infiltration, the inoculated plants are inspected for signs of water soaking.

The inoculum suspension is prepared by triturating up to 1.0 g vacuum-dried, TMGMV-infected Turkish Samsun nn tobacco leaf tissue in 1-50 ml of sodium phosphate buffer (pH 7.2). The extracted samples are then filtered by means known in the art, for example, strained through sterile cheesecloth into capped vials. At the time of inoculation, the virus-buffer mixture is poured into 1 liter of sterile deionized water. One gram of carborundum (320 grit) was added to each liter to serve as an abrasive.

The application methods consist of over-the-top spraying application for infiltration including for example, without limitation, the aid of a $CO_2$-propelled backpack sprayer or tractor mounted sprayers. An over-the-top sprayer can be set at any appropriate pressure including at a pressure less than 400 p.s.i. Preferably, the over-the-top sprayer is set at a pressure between 20 and 100 p.s.i. More preferably, the over-the-top sprayer is set at a pressure less than 20 p.s.i. In other embodiments, the over-the-top sprayer is set at a pressure greater than 400 p.s.i.

A related method of application according to the subject invention includes applying the inoculum described above to TSA plants that are simultaneously injured. Injury of TSA plants may be administered using a variety of methods known to the skilled artisan including, for example, a mechanical device such as a chain-link fence or carpet dragged behind a tractor or mowing the plants prior to applying the inoculum suspension.

Inoculum suspension production for the following field applications can preferably include the steps of (1) growing susceptible tobacco plants (i.e., Nicotiana tabacum, cv. Samsun nn) from seeds to seedlings in a greenhouse (4-6 weeks); (2) transplanting the seedlings to pots (15-cm diameter; 4-liter), with one plant per pot; (3) after 1-2 weeks, inoculating the potted plants with TMGMV inoculum from TGMV-infected tobacco tissue; (4) 12 weeks after inoculation, harvesting the leaves and homogenizing 1:1 (w/v) in sterile, deionized water using known methods for extracting sap (i.e., blender); (5) filtering the extracted sap using known methods (i.e., filtering the sap through a cheesecloth) to provide a TMGMV inoculum in accordance with the present invention. The TMGMV inoculum can be stored frozen at −20° C. in non-reactive containers (i.e., plastic bottles) until use. Inoculum stored in this manner remains highly infective for at least 5 months. In a preferred embodiment, the inoculum stored in this manner remains highly infective from about 6 months to two years.

Using the inoculum suspension described above, seven methods of inoculation including various means of abrasion are tested in field trials to establish efficiency and feasibility of delivery methods of TMGMV. Appropriate controls are included for comparisons.

For manual (or hand-) inoculation, TSA leaves (3-5 per plant) are hand-rubbed (abraded) with a piece of cheesecloth soaked in the TMGMV inoculum, prepared as described above. For leaf-infiltration, TSA leaves (3-5 per plant) are infiltrated with the TMGMV inoculum, prepared as described above, with the aid of a low-pressure (20 psi) backpack sprayer. The sprayer nozzle is placed on the adaxial leaf surface and the TMGMV inoculum (about 1 ml) forced into the leaf tissue.

Figures 11A, 11B, 11C, 11D, 11E:
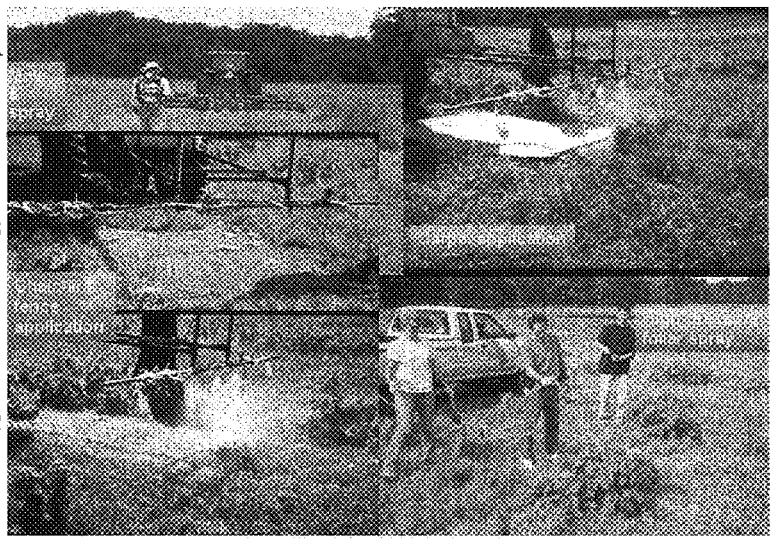
FIGS. 11A-11E are photographs depicting various methods for inoculating plants with TMGMV in accordance with the present invention.

With regard to over-the-top spray (or foliar spray), the TMGMV inoculum is sprayed over TSA foliage with a backpack sprayer at 20 psi at the rate of 100 ml per $m^2$ (or approximately 100 gallons per acre). Mow-and-spray applications consist of mowing TSA plants to a height of 10-12 cm above the soil surface and immediately spraying the cut stems with the TMGMV inoculum using a backpack sprayer, for example, at 20 psi and at the rate of 100 ml per $m^2$, as illustrated in FIG. 11A. Of course, with this and other methods, other pressures and rates could be used, or desired.

With the abrasion-and-spray application (i.e., chain-link fence application or carpet application), TSA plants are abraded by dragging over the TSA plants a 4-foot-by-4-foot piece of chain-link fencing using a tractor and simultaneously sprayed with the TMGMV inoculum using a tractor-mounted spray boom set at 20 psi at the rate of 50 gallons per acre, as illustrated in FIGS. 11B and 11C. Alternatively, TSA plants can be abraded by dragging over the TSA plants a 4-foot-by-4-foot piece of carpet using a tractor and simultaneously sprayed with the TMGMV inoculum using a tractor-mounted spray boom set at 20 psi at the rate of 50 gallons per acre, as illustrated in FIG. 11D.

For high-pressure spray of at least 400 psi, TSA plants are sprayed with the TMGMV inoculum for approximately 5 seconds per plant with the aid of a high-pressure sprayer, as illustrated in FIG. 11E. The results of these field trials for testing inoculation methods are provided in the following Table 8.

The efficacy of TMGMV as a control for TSA is confirmed in replicated and repeated field trials in eight locations in six Florida counties, as provided in Table 8. The objective of conducting these field trials is to evaluate the different application methods with two inoculum dilutions, 1:10 and 1:50 w:v. Plants growing under two different conditions, in open pastures and under trees in hammocks, are used in different trials. Before inoculation, the stored TMGMV inoculum (as described above), is thawed and diluted in 0.02M sodium phosphate buffer (pH 7.2) to yield 1:10 and 1:50 v:v dilutions.

TABLE 8

Effectiveness of Seven Different Methods of Inoculation of TMGMV: Results from Field Trials

| Application method | Trial No. | % TSA kill (days post-inoc.)[a] | |
|---|---|---|---|
| | | Control | Inoculated |
| Hand-inoculation | 1 | 22.0[b] | 67.0 (49) |
| | 2 | 17.0 | 63.0 (49) |
| Leaf-infiltration, 20 psi | 1 | 5.7 | 59.7 (14)[c] |
| | 2 | 1.6 | 88.4 (51) |
| Leaf-infiltration, 20 psi | Alachua County 1 | 0.0 | 93.0 (42) |
| | Alachua County 2 | 0.0 | 97.0 (60) |
| Foliar spray, 20 psi | Hendry County | 32.0 | 35 (49)[NS] |
| Foliar spray, 20 psi | Highlands County | 7.0 | 40.0 (49) |
| Mow and spray, 20 psi | Hendry County | 27.0 | 27.0 (49)[NS] |
| Mow and spray, 20 psi | Highlands County | 37.0 | 45.0 (49)[NS] |
| Chain-link fence application | Highlands County | 0.0 | 73.3 (51) |
| Chain-link fence application | Brevard County | 0.0 | 78.0 (63) |
| Carpet application | Highlands County | 0.0 | 88.2 (51) |
| Carpet application | Brevard Country | 0.0 | 68.0 (63) |
| High-pressure spray | Sumter County | 0.0 | 99.0 (78) |
| High-pressure spray | Brevard County | 0.0 | 98.0 (65) |

[a]Differences between control and inoculated treatments significant at 95% or 99% level of confidence, except as noted. NS = results not significant between the control and inoculated treatments.
[b]Control plants in some trials died at noticeable numbers due to severe drought or flooding at the sites.
[c]This trial was abandoned after 14 days because of disruption from cattle and flooding at the site.

Figures 12A, 12B:
FIGS. 12A-12B are photographs depicting TSA reaction to inoculation with TMGMV in the field, in accordance with the present invention.

Typically, the inoculated plants do not demonstrate any reaction to the TMGMV inoculum for up to three weeks, as illustrated in FIG. 12A. Between the third and fourth weeks, the plants start to wilt noticeably, as illustrated in FIG. 12B and die rapidly and completely without regrowth from roots.

As illustrated in Table 8, the application methods involving abrasion-and-spray (both chain-link fence application and carpet application) and high-pressure spray are the most feasible for field application. Best results (98-99% control) are obtained with the high-pressure spray application followed by the chain-link fence and carpet application methods (76% control). Mow-and-spray application and low-pressure, over-the-top spray methods are less effective (<45% control). Leaf-infiltration and manual inoculation methods, although effective (85% and 65% control, respectively), may not be particularly practical for field use.

Thus, TMGMV-infected TSA plants die as a result of a rapid hypersensitive response of the plant to the infection. Unlike susceptible tobacco plants that develop systemic mild green mosaic symptoms from TMGMV infection but do not die, TSA plants die suddenly, at about 3 weeks after inoculation, without expressing mosaic symptoms. This type of hypersensitivity of TSA to TMGMV can be exploited in a TMGMV-based bioherbicide.

Mechanism of Systemic Hypersensitive Killing of TSA

Hypersensitive response (HR) can be described as a race between the speed of virus replication and movement within the plant, and the speed of plant defense response in confining the virus. Plant death, as seen in TSA inoculated with TMGMV, is the manifestation of the virus having won the race. The hypersensitive response is an active response in which the plant recognizes the pathogen and responds defensively in an attempt to confine the pathogen to the initial infection area. The hypersensitive response normally results in localized cell death. Complete or near complete death of the whole plant, as is seen in the TSA-TMGMV system, is rare. Based on the recent isolation and description of HR-type resistance genes, the R genes, and pathogen avirulence genes, avr genes in other plant pathogen systems, the trigger of the hypersensitive response is a specific interaction between a receptor domain of the R gene product and a specific pathogen elicitor, a product of the avirulence gene. Different forms of the elicitor can interact differently with the resistance gene. Strong elicitors induce the resistance response quickly, with the pathogen then being confined to a small area surrounding the initial infection site. Weak elicitors slowly induce the hypersensitive response, allowing the pathogen to spread further before it is confined, if at all. These differences are probably due to the availability or affinity of the elicitor to the receptor. Thus, viral elicitors appear to be any viral product that the plant can recognize in order to mobilize a resistance response (Dawson, 1999; Chisholn et al., 2000). Different plants recognize the same viral gene product in a different manner. Conversely, viruses evolve by generating viral gene products that escape host recognition and thus avoid the hypersensitive response that limits their ability to systemically infect the host (Dawson, 1999).

All tobamoviral gene products have been shown to act as an elicitor in some plant. The tobamovirus coat protein was the first viral gene product recognized as an elicitor of an hypersensitive response in tobacco containing the N gene, (Saito et al., 1987). The movement protein gene product has been mapped as the elicitor of the hypersensitive response in tomato containing TM-2 and TM-$2^2$ genes, (Weber and Pfitzner, 1998). N-gene-mediated hypersensitive response in tobacco is induced by the tobamovirus replicase. (Padgett et al., 1997).

Several techniques have proven highly effective in identifying viral factors responsible for elicitation of the hypersensitive response. The first is the production of chimeric viruses consisting of genomic segments from different viruses. This method is particularly useful in systems with closely related viruses that have distinct host resistance phenotypes. In many systems, however, both resistance inducing and/or noninducing viruses do not exist. To overcome this problem, heterologous viral vectors can be produced and used for the expression of specific viral components in attempts to assign avirulence functions (Culver, 1997; Shivprasad et al., 1999).

The induction of the hypersensitive response in plants does not necessarily require the presence of the pathogen responsible for the elicitor. Culver and Dawson (1991) showed that TMV coat protein expression alone in transgenic tobacco containing the N gene produced the hypersensitive phenotype. Erickson et al. (1999) showed that helicase domain of the TMV replicase proteins induces N-mediated defense response in tobacco in the absence of virus replication. Also, Duan et al. (1999), using a transient expression system demonstrated that a single, host-specific bacterial pathogenicity gene elicited, in the absence of the pathogen, host-specific symptoms diagnostic of the disease caused by the bacterial pathogen. The ability of an elicitor to induce the hypersensitive response in certain plants would eliminate the need to utilize the intact virus. Therefore, the TMGMV elicitor alone can be used as an herbicide.

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

REFERENCES

Akanda, R. U., Dowler, C. C., Mullahey, J. J., and Shilling, D. G. 1997. Influence of postemergence herbicides on tropical soda apple (*Solanum viarum*) and Bahiagrass (*Paspalum notatum*). Weed Technol. 11:656-661.

Chisholm, S. T., Mahajan, S. J., Whitham, S. A., Yamamoto, M. L. and Carrington, J. C. 2000. Cloning of the Arabidopsis RTM1 gene, which controls restriction of long-distance movement of tobacco etch virus. Proc. Natl. Acad. Sci. 97: 489-494.

Culver, J. N. 1997. Viral avirulence genes. Chapter 6. Pages 196-219 in: G. Stacey and N. T. Keen, eds. Plant-Microbe Interactions, Vol. 2. Chapman & Hall, New York.

Culver, J. N., and Dawson, W. O. 1991. Tobacco mosaic virus elicitor coat protein genes produce a hypersensitive phenotype in transgenic *Nicotiana sylvestris* plants. Mol. Plant-Microbe Interact. 4:458-463.

Dawson, W. O. 1999. Tobacco mosaic virus virulence and avirulence. Phil. Trans. R. Soc. Lond. B 354:643-651.

Duan, Y. P., Castañeda, A., Zhao, G., Erdos, G., Gabriel, D. W. 1999. Expression of a single, host specific, bacterial pathogenicity gene in plant cells elicits division, enlargement, and cell death. Molec. Plant-Microbe Interact. 12:556-560.

Erickson, F. L., Holzberg, S., Calderon-Urrea, A., Handley, V., Axtell, M., Corr, C., and Baker, B. 1999. The helicase domain of the TMV replicase proteins induces the N-mediated defense response in tobacco. Plant Journal 18, 67-75.

McGovern, R. J., Polston, J. E., and Mullahey, J. J. 1994. *Solanum viarum* Dunal: weed reservoir of plant viruses in Florida. Int. J. Pest Manage. 40:270-273.

Mullahey J. J. 1996. Tropical soda apple (*Solanum viarum* Dunal), a biological pollutant threatening Florida. Castanea 61:255-260.

Padgett, H. S. Watanabe, Y., and Beachy, R. N. 1997. Identification of the TMV replicase sequence that activates the N gene-mediated hypersensitive response. Mol. Plant-Microbe Interact. 10:709-715.

Purcifull, D. E. 1990. Ouchterlony double-diffusion tests in the presence of sodium dodecyl sulfate for detection of virion proteins and virus-induced inclusion proteins. Pages 179-196 in: R. Hampton, E. Ball, and S. De Boer, eds., Serological Methods for the Detection and Identification of Viral and Bacterial Plant Pathogens, APS Press, St. Paul, Minn.

Saito, T., Meshi, T., Takamatsu, N., and Okado, Y. 1987. Coat protein gene sequences of tobacco mosaic virus encodes host response determinant. Proc. Natl. Acad. Sci. USA 85:6074-6077.

Shivprasad, S., Pogue, G. P., Lewandowski, J., Hidalgo, J., Donson, J., Grill, L. K., and Dawson, W. O. 1999. Heterologous sequences greatly affect foreign gene expression in tobacco mosaic virus-based vectors. Virology 255:312-323.

Weber, H. and Pfitzner, J. P. 1998. Tm-$2^2$ resistance in tomato requires recognition of the carboxy terminus of the movement protein of tomato mosaic virus. Molec. Plant-Microbe Interact. 11:498-503.

We claim:

1. A method of inducing lethal hypersensitive response in tropical soda apple plants comprising the steps of:
    (a) obtaining an inoculation suspension comprising Tobacco Mild Green Mosaic Virus;
    (b) applying said inoculation suspension to a few leaves of the tropical soda plant by manual inoculation.

2. The method of claim 1 wherein said inoculation suspension includes a buffer and water.

3. The method of claim 2, wherein the buffer is sodium phosphate.

4. The method of claim 2, wherein said obtaining step comprises extracting the Tobacco Mild Green Mosaic Virus from tissue of a host plant in water; filtering the extraction; and freezing the filtered extraction.

5. The method of claim 4, wherein said host plant is a tobacco plant susceptible to the Tobacco Mild Green Mosaic Virus.

6. The method of claim 5, wherein said tobacco plant is *Nicotiana tabacum*.

7. The method of claim 4, wherein said extracting step comprises harvesting host plant tissue and placing the tissue in the water in a blender.

8. The method of claim 4, wherein the obtaining step further comprises the step of diluting the extraction with the buffer prior to application on the tropical soda apple plants leaves.

9. The method of claim 1 wherein said manual inoculation is performed using cheesecloth.

10. A method of inducing lethal hypersensitive response in tropical soda apple plants comprising the steps of:
    (a) obtaining an inoculation suspension comprising Tobacco Mild Green Mosaic Virus;
    (b) applying said inoculation suspension to a few leaves of the tropical soda plant by spray application.

11. The method of claim 10 wherein said inoculation suspension includes a buffer and water.

12. The method of claim 11, wherein the buffer is sodium phosphate.

13. The method of claim 11, wherein said obtaining step comprises extracting the Tobacco Mild Green Mosaic Virus from tissue of a host plant in water; filtering the extraction; and freezing the filtered extraction.

14. The method of claim 13, wherein said host plant is a tobacco plant susceptible to the Tobacco Mild Green Mosaic Virus.

15. The method of claim 13, wherein said tobacco plant is *Nicotiana tabacum*.

16. The method of claim 13, wherein said extracting step comprises harvesting host plant tissue and placing the tissue in the water in a blender.

17. The method of claim 13, wherein the obtaining step further comprises the step of diluting the extraction with the buffer prior to application on the tropical soda apple plants leaves.

18. The method of claim 10, wherein the spray application is provided at a pressure of 400 p.s.i. or greater.

19. The method of claim 18, wherein said spray application is provided by a sprayer that is operated from a vehicle.

20. The method of claim 19, further comprising the step of injuring the tropical soda plants leaves prior to applying said inoculation suspension.

21. The method of claim 20, wherein said injuring the tropical soda plants leaves comprises mowing the plants.

22. The method of claim 20, wherein said injuring the tropical soda plants leaves comprises dragging a chain-link fence over the plants.

23. The method of claim 20, wherein said injuring the tropical soda plants leaves comprises dragging a carpet over the plants.

24. The method of claim 10, wherein the spray application is provided at a pressure of 400 p.s.i. or less.

25. The method of claim 24, wherein the spray application is provided at a pressure of between 20 and 100 p.s.i.

26. The method of claim 24, wherein said spray application is provided by a sprayer that is operated from a vehicle.

27. The method of claim 24, wherein said spray application is provided at a pressure of 20 p.s.i. or less.

28. The method of claim 27, wherein said spray application is provided by a backpack sprayer.

29. The method of claim 28, further comprising the step of injuring the tropical soda plants leaves prior to applying said inoculation suspension.

30. The method of claim 29, wherein said injuring the tropical soda plants leaves comprises mowing the plants.

31. The method of claim 29, wherein said injuring the tropical soda plants leaves comprises dragging a chain-link fence over the plants.

32. The method of claim 29, wherein said injuring the tropical soda plants leaves comprises dragging a carpet over the plants.

* * * * *

UNITED STATES PATENT AND TRADEMARK OFFICE
CERTIFICATE OF CORRECTION

PATENT NO. : 7,494,955 B2
APPLICATION NO. : 10/755008
DATED : February 24, 2009
INVENTOR(S) : Raghavan Charudattan, Matthew Scott Pettersen and Ernest Hiebert It is certified that error appears in the above-identified patent and that said Letters Patent is hereby corrected as shown below:

Column 1,
Line 54, "The a typical" should read --The atypical--.

Column 9,
Line 28, "*C. annuum* L. (Jalapeno)" should read --*C. annuum* L. (Jalapeño)--.
Line 57, "indirect ELSIA" should read --indirect ELISA--.

Column 10,
Lines 4-5, "Jalapefño)" should read --Jalapeño)--.

Column 15,
Line 50, "Chisholn et al." should read --Chisholm et al.--.

Signed and Sealed this

Fifteenth Day of September, 2009

David J. Kappos
*Director of the United States Patent and Trademark Office*